(12) United States Patent
Stelter et al.

(10) Patent No.: US 7,393,357 B2
(45) Date of Patent: Jul. 1, 2008

(54) ENDOVASCULAR STENT GRAFT

(75) Inventors: Wolf Stelter, Bad Soden (DE); Michael Lawrence-Brown, Floreat (AU); David Hartley, Subiaco (AU)

(73) Assignees: Cook Incorporated, Bloomington, IN (US); William Cook Europe ApS, Bjaeverskov (DK); William A. Cook Australia Pty. Ltd., Brisbane (AU)

( * ) Notice: Subject to any disclaimer, the term of this patent is extended or adjusted under 35 U.S.C. 154(b) by 698 days.

(21) Appl. No.: 10/783,401

(22) Filed: Feb. 20, 2004

(65) Prior Publication Data
US 2004/0260383 A1 Dec. 23, 2004

Related U.S. Application Data

(62) Division of application No. 09/808,251, filed on Mar. 14, 2001, now Pat. No. 6,695,875.

(60) Provisional application No. 60/202,468, filed on May 8, 2000, provisional application No. 60/189,114, filed on Mar. 14, 2000.

(51) Int. Cl.
*A61F 2/06* (2006.01)
(52) U.S. Cl. ..................... 623/1.11; 606/108

(58) Field of Classification Search .................. 623/1.35
See application file for complete search history.

(56) References Cited

U.S. PATENT DOCUMENTS 5,676,696 A * 10/1997 Marcade ..................... 623/1.35
6,183,481 B1 * 2/2001 Lee et al. .................... 606/108

FOREIGN PATENT DOCUMENTS

WO WO 99/43378 * 9/1999

* cited by examiner

*Primary Examiner*—Corrine McDermott
*Assistant Examiner*—Christopher D Prone
(74) *Attorney, Agent, or Firm*—Richard J. Godlewski

(57) ABSTRACT

An endovascular stent graft assembly (10) for use with abdominal aorta aneurysms (70) and having a main stent graft body (12) and a separate attachment graft tube (14) that extends proximally therefrom having the proximal attachment stent (50) thereon for infrarenal attachment of the assembly (10) to the aorta (74). A distal end portion (44) of the attachment graft tube (14) underlies the proximal end portion (30) of the main stent graft body (12) and presses outwardly there against forming a friction fit, at an overlapping region (64). The main stent graft body (12) has an ipsilateral leg (22) and a contralateral stump (24) at the bifurcation (26). After deployment of the attachment graft tube (14), the contralateral leg (16) is deployed at the contralateral stump to complete the stent graft assembly (10).

4 Claims, 9 Drawing Sheets

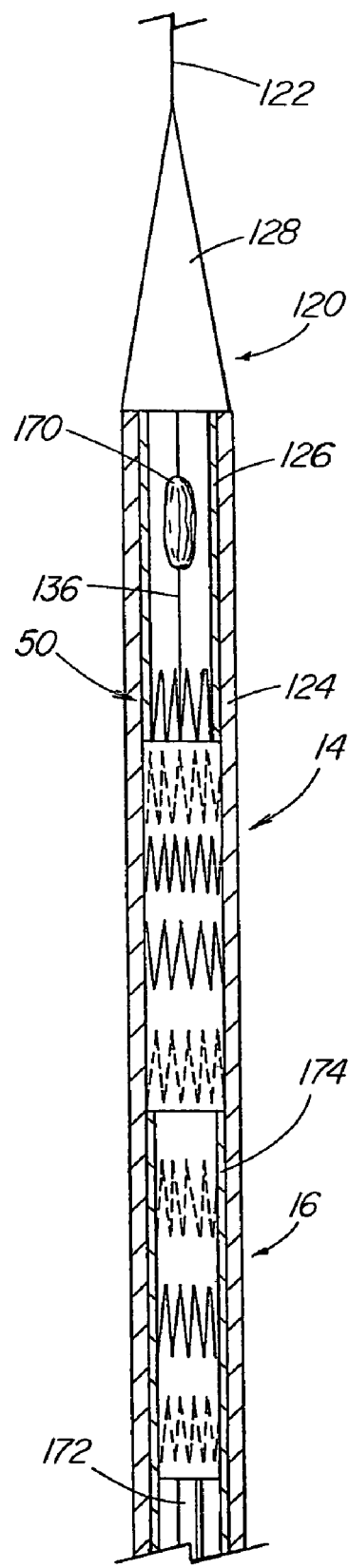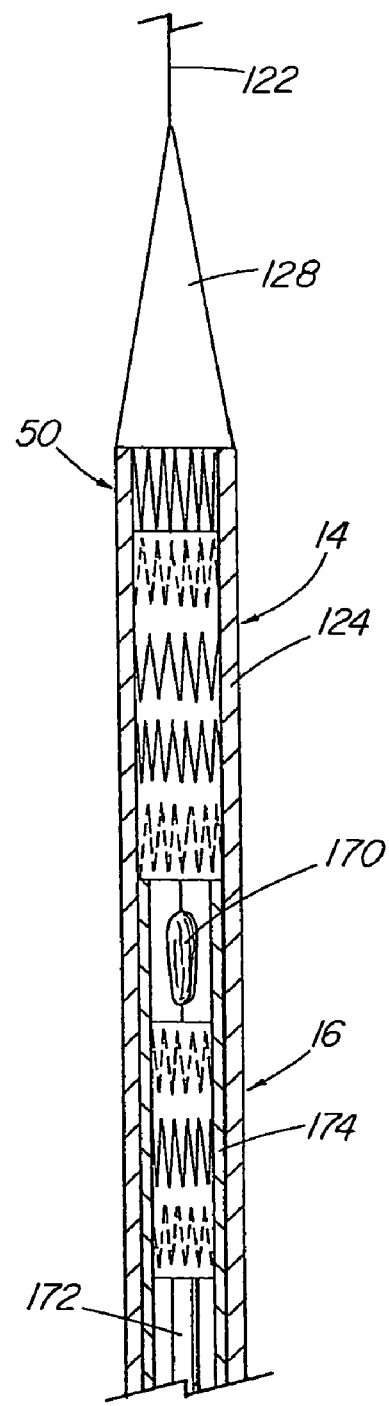
FIG. 13
FIG. 14

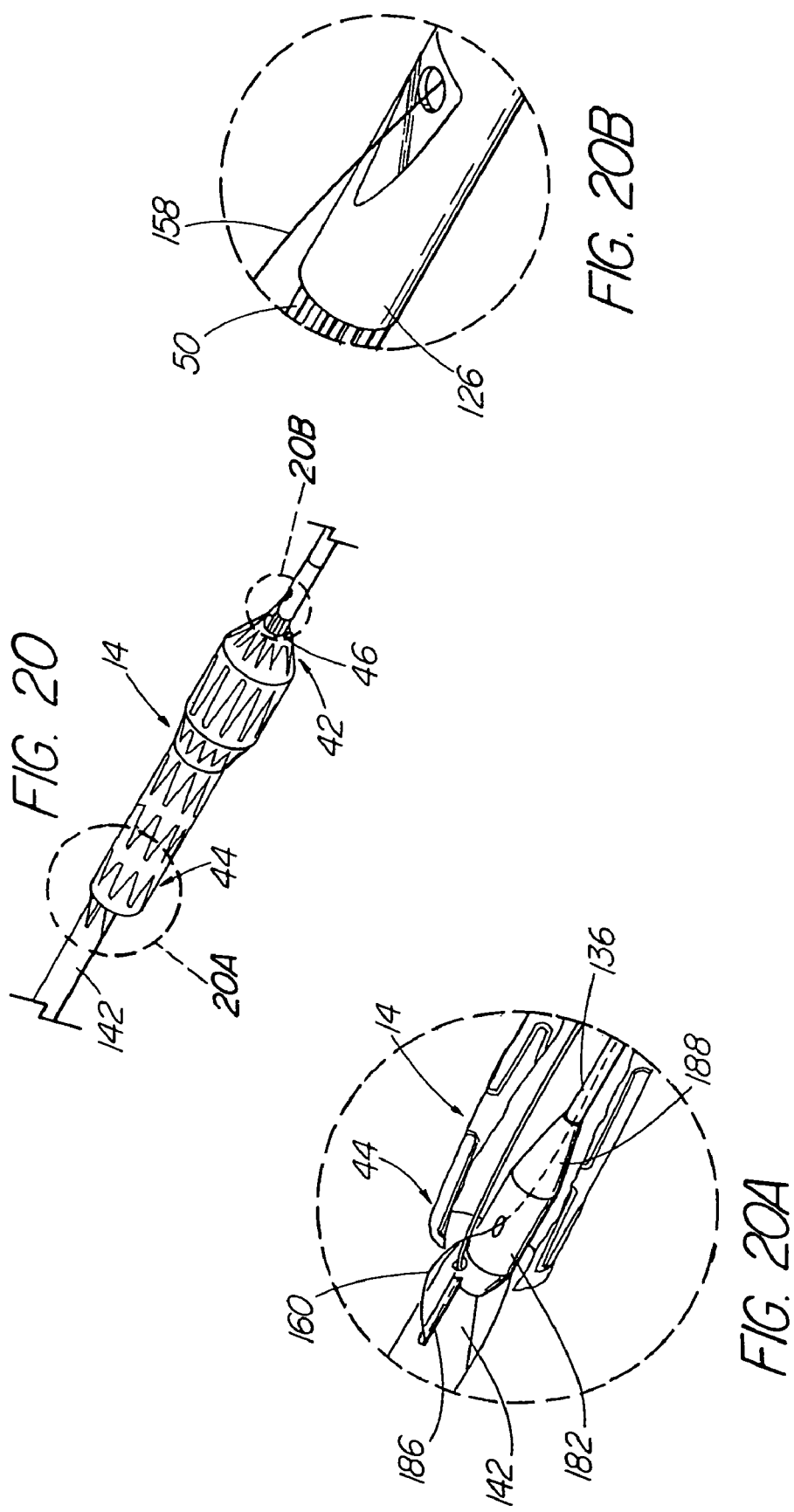

ENDOVASCULAR STENT GRAFT

RELATED APPLICATION INFORMATION

This is a Divisional of U.S. patent application Ser. No. 09/808,251 filed Mar. 14, 2001, now U.S. Pat. No. 6,695,875 which, in turn, claims priority to U.S. Provisional Application Ser. No. 60/189,114 filed Mar. 14, 2000 and Provisional Application Ser. No. 60/202,468 filed May 8, 2000.

TECHNICAL FIELD

The present invention relates to medical devices and more particularly to endovascular devices.

BACKGROUND OF THE INVENTION

In recent years treatment of aneurysms has included the use of stent grafts that are emplaced within the vascular networks and that include one or more stents affixed to graft material. The stent grafts are secured at a treatment site by endovascular insertion utilizing introducers and catheters, whereafter they are enlarged radially and remain in place by self-attachment to the vessel wall. In particular, stent grafts are known for use in treating descending thoracic and abdominal aortic aneurysms where the stent graft at one end defines a single lumen for placement within the aorta and at the other end is bifurcated to define two lumens, for extending into the branch arteries.

One example of such a stent graft is disclosed in PCT Publication No. WO 98/53761 in which the stent graft includes a sleeve or tube of biocompatible graft material such as Dacron™ polyester fabric (trademark of E. I. DuPont de Nemours and Co.) or polytetrafluoroethylene defining a lumen, and further includes several stents secured therealong, with the stent graft spanning the aneurysm extending along the aorta proximally from the two iliac arteries; the reference also discloses the manner of deploying the stent graft in the patient utilizing an introducer assembly. The graft material-covered portion of the single-lumen proximal end of the stent graft bears against the wall of the aorta above the aneurysm to seal the aneurysm at a location that is spaced distally of the entrances to the renal arteries. Thin wire struts of a proximal stent extension traverse the renal artery entrances without occluding them, since no graft material is utilized along the proximal stent while securing the stent graft in position within the aorta when the stent self-expands. An extension is affixed to one of the legs of the stent graft to extend along a respective iliac artery and, optionally, extensions may be affixed to both legs. Another known stent graft is the Zenith AAA™ stent graft sold by William A. Cook Australia Pty., Brisbane, Australia.

In prior art stent grafts, graft fixation was achieved by fixation at the top or proximal end by barbs or by a stent portion that is uncovered by graft material and could be incorporated into the vessel wall. Distal end fixation was attained by friction within the branch or iliac arteries. The stents of the prior art stent grafts tended to be flexible and relatively soft. The proximal main tube graft was of a standardized length, and that length tended to be significantly shorter than the aneurysms themselves, while the full length was bridged and achieved by smaller diameter extensions or legs.

With the prior art stent grafts, certain late complications were common: due to the above-mentioned configuration there was a certain instability leading to kinking, obstruction of the lumen and/or disintegration leading to possible graft explantation, wherein the stent graft undesirably moved out of its intended position mostly due to larger displacement forces within the smaller diameter stent graft portions; material fatigue also occurred, leading to endoleak wherein blood flow continued into the aneurysm.

SUMMARY OF THE PRESENT INVENTION

The foregoing problems are solved and a technical advance is achieved in the stent graft of the present invention. The stent graft assembly of the present invention includes a main stent graft device or body with an integral ipsilateral leg and a contralateral stump that together define a bifurcation at the distal end, includes a contralateral extension, and further includes an attachment graft tube. The main stent graft body and the attachment tube at its proximal end, will together span the whole aneurysm, but the main stent graft body itself is selected to have a length that is less than the span of the aneurysm, measured proximally from the bifurcation of its ipsilateral limb and the contralateral stump. The proximal end of the main stent graft body is adapted to remain unattached to the vessel wall, unlike conventional stent grafts, but the attachment tube proximal end includes an attachment stent for vessel wall attachment at the aneurysm proximal neck, with the attachment tube fully sealing relative to the aorta while permitting free flow to the renal arteries. Furthermore, in contrast to the prior systems which started positioning at the top, proximally at the renal arteries, the main graft assembly is built starting from below at the distal bifurcation first and extending then from distal to proximal to the renal orifices at the aneurysm's proximal neck.

After partial deployment wherein the contralateral stump is released from the delivery system sheath, the main stent graft body bifurcation is seated against the aortic vessel wall at the iliac arteries bifurcation, prior to deployment of the ipsilateral leg from the delivery system sheath. The second or attachment graft tube of selected length then is brought up contralaterally through the main stent graft body. The attachment tube is then deployed such that a distal portion of substantial length remains within the proximal end of the main stent graft body to define an overlap region, and an attachment stent extending from the proximal end of the attachment tube is then deployed to attach to the vessel wall at the proximal neck of the aneurysm at the renal arteries. The overlap region may be as little as 2 mm to 5 mm in length but is preferably at least about 20 mm and there is a friction fit between the attachment graft tube distal portion and the main stent graft body proximal portion upon full deployment (expansion) of the stents of the attachment tube. The contralateral limb is thereafter moved into position and affixed to the contralateral stump. Preferably, both the attachment graft tube and the contralateral limb are delivered in a second double-sheath delivery system, through the contralateral artery. Such an overlapping double tube result at the proximal end of the main stent graft body is stronger, and the position of the stent graft assembly after full deployment is more stable against explantation.

Optionally, a third or intragraft tube is placeable into the main stent graft body to underlie and extend in both directions beyond the overlapping region between the main stent graft device and the attachment graft tube. The third graft tube would expand to define a friction fit within both the attachment graft tube and the main stent graft body and have a length greater than the overlap region, thus strengthening the friction fit between the attachment graft tube and the main stent graft body. Such third graft tube would be utilized should configuration changes of the aneurysm, and the subsequent increase in the distance between the renal arteries and the bifurcation, tend to pull the attachment graft tube partially from the main stent graft body and decrease the overlap region therebetween; such intragraft tube can be easily placed during a subsequent procedure.

The present invention is also directed to a first graft member (corresponding to the attachment tube discussed hereinabove) that is to be used in conjunction with at least one other graft member (the main graft tube), and that includes an attachment region having an attachment stent for attachment to a vessel wall, and a distal portion defining another attachment region for attachment to the at least one other graft member.

The present invention includes method aspects: a method of placing an endovascular stent graft in a vessel at a bifurcation thereof where branch vessels join the vessel, for treating an aneurysm thereat, comprising the steps of placing a bifurcated main stent graft body in the aneurysm unattached to a wall of the vessel with a first leg portion in a first branch vessel; urging a bifurcation of the main stent graft body into a seated position against the bifurcation of the vessel to move a second leg portion in a second branch vessel; and securing the stent graft to the vessel wall.

In an additional aspect, the present invention includes a delivery system for endovascular devices, comprising a first sheath having a distal end and a proximal end and containing at least a first expandable device at a proximal end; a second sheath movable within the first sheath and having a respective distal end and a respective proximal end, the respective proximal end concluding distally of the first expandable device and containing a second expandable device; a first pusher associated with the first expandable device extending thereto within the first and second sheathes from a first proximal control pusher end exposed at the distal ends of the first and second sheathes; and a second pusher associated with the second expandable device extending thereto within the first and second sheathes from a second distal control pusher end exposed at the distal ends of the first and second sheathes.

BRIEF DESCRIPTION OF THE DRAWINGS

An embodiment of the present invention will now be described byway of example with reference to the accompanying drawings, in which:

FIGS. 5 to 7 show the sequence of steps in the delivery of the stent graft arrangement of the present invention, in which FIG. 5 shows the main stent graft device being positioned and partially deployed in the aneurysm and seated onto the vessel wall bifurcation; FIG. 6 illustrates the introduction the second double-sheath delivery system into the main stent graft body; and FIG. 7 shows the deployment of the attachment tube and contralateral extension;

FIG. 13 illustrates the second double-sheath delivery system containing the attachment tube and the contralateral leg and their respective pushers;

FIG. 14 shows another version of the second double-sheath delivery system in which the inflation balloon follows the attachment tube in the system;

FIG. 20 shows enlargements (FIGS. 20A and 20B) of the trigger wire containment arrangement for the attachment stent of the attachment tube and for the distal end portion of the main body.

DETAILED DESCRIPTION

Figure 1:
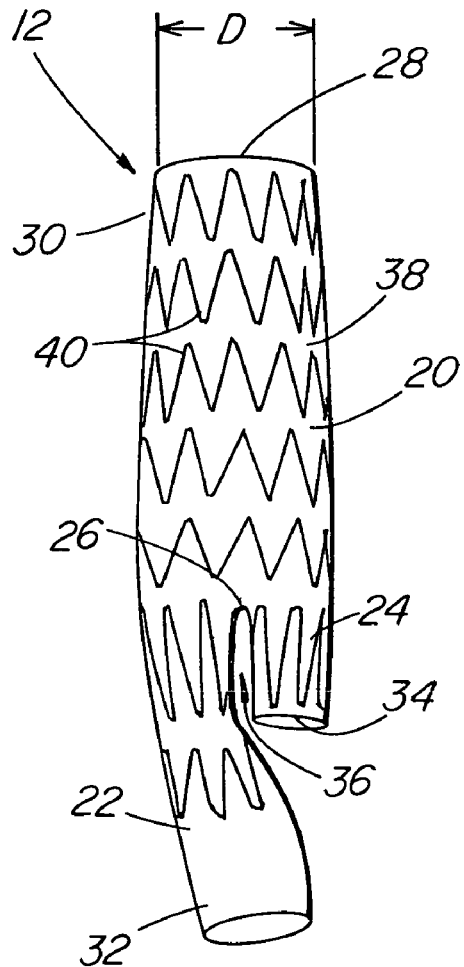
FIG. 1 illustrates the main stent graft device, having a main body, an ipsilateral leg and a contralateral stump.
Figure 2:
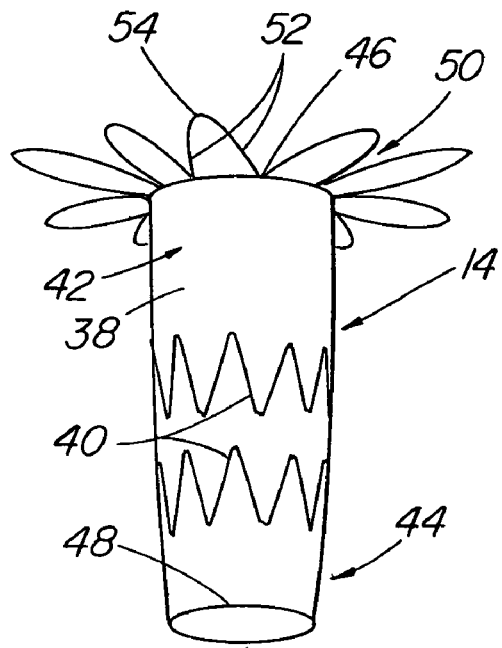
FIG. 2 illustrates an attachment tube of the present invention, with a proximal end exposed beyond the graft material and whose length can vary depending upon the length of the aneurysm.
Figure 3:
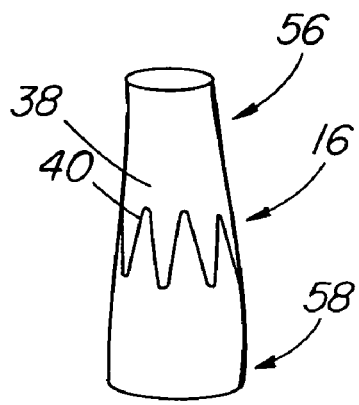
FIG. 3 shows a contralateral leg for affixing to the contralateral stump, and having a flared distal end.
Figure 4:
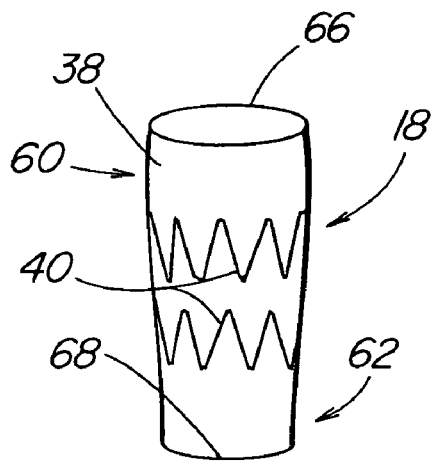
FIG. 4 illustrates an additional intragraft tube for within the lumen of the main stent graft body and the attachment tube for spanning and supporting the overlapping region therebetween.

The stent graft assembly of the present invention includes a main stent graft body or device 12, a second graft body or attachment tube 14, and a contralateral limb extension graft 16, as seen in FIGS. 1 to 3 in their fully expanded state, if unconstrained within a vessel or delivery catheter. FIG. 4 shows an optional but preferred additional, intragraft tube graft body 18. Main stent graft body 12 includes a primary graft section 20, an ipsilateral leg 22 and a contralateral limb or stump 24. Primary graft section 20 is disposed within the aneurysm and extends from the bifurcation 26 to a proximal end 28 of proximal end portion 30, and has a lumen with a relatively constant diameter D that approximates the diameter of a healthy section of the aorta, generally about 26 mm. Ipsilateral leg 22 is associated with the ipsilateral iliac artery and extends to a distal end or cuff 32 that is flared. Contralateral stump 24 is associated with the contralateral iliac artery and coextends a short distance from bifurcation 26 to a distal end 34; preferably, it is spaced from ipsilateral leg 22 a distinct small gap 36 therefrom for the length of the contralateral stump.

Main stent graft body 12, attachment tube 14, contralateral limb 16 and intragraft tube 18 all comprise graft material 38 and a plurality of self-expanding stents 40 that are secured to and along the graft material either along the outer surface or inner surface of the graft material such as by sutures. At cuff 32 of ipsilateral limb 22 of main stent graft body 12, a stent is secured to the inner surface of the graft material while the stent along the proximal end portion 30 may be secured to the outer surface. Along the proximal and distal end portions 42,44 of the graft material of attachment tube 14, the respective stents adjacent to proximal and distal ends 46,48 are secured to the inner surface. An attachment stent 50 is secured to the proximal end 46 of attachment tube 14 containing pairs of struts 52 shown joined at ends 54 that are adapted such as with barbs to lock to the vessel wall of the aorta, and being so fabricated as to be spring biased for the ends 54 to tend to diverge and expand laterally to press against the vessel wall upon release at deployment. Proximal and distal end portions 56,58 of contralateral limb 16 include stents secured along the inner surface of the stent graft material, with distal end portion 58 preferably being a cuff similar to cuff 32 of ipsilateral limb 22. Regarding intragraft tube 18, proximal and distal end portions 60,62 include stents that are secured along the inner surface of the graft material, while one or two (as shown) or more stents 40 may be secured to the outer surface of the intermediate region, or may be secured along the inner surface, if desired.

Preferably, the main stent graft device 12 would have a primary graft section 20 with a proximal lumen about 24 mm in diameter and extending about 50 mm in length to the bifurcation. The ipsilateral leg 22 is about 12 mm in diameter and continues along a length about 80 mm from the bifurcation 26 to a flared distal end or cuff 32 about 16 to 18 mm in diameter when unconstrained. A contralateral stump 24 coextends along the ipsilateral leg and also has a diameter of about 12 mm with a length of about 35 mm. Preferably, the length of the contralateral stump 24 is spaced from the ipsilateral leg 22 (gap 36) to easily be fitted over and seated against the bifurcation of the vessel at the iliac arteries, when the main stent graft body is pulled distally after partial deployment, that is, wherein the contralateral stump exits the delivery sheath (see FIG. 6) and is deflected laterally upon expansion of stents 40 that have also exited the sheath after the sheath has been partially withdrawn distally.

Attachment tube 14 should have a diameter of about 26 mm, 28 mm or 30 mm or greater when unconstrained, and could have one of several selected lengths, with attachment stent 50 exposed about 15 mm or so beyond the proximal end 46 of the stent graft material. Distal end portion 44 would be overlapped by the proximal end portion 30 of the main stent graft device 12 and would be at least about 20 mm in length within the proximal end portion 30. For most aneurysms, the attachment tube length would be about 70 mm between proximal and distal ends 46,48, of which the overlap length would be at least 20 mm; for larger aneurysms the attachment tube length would be about 85 mm; and for smaller aneurysms, the length of the attachment tube could be about 50 mm. Whenever the longest possible overlap is desired with the main stent graft device, the longest attachment tube should be utilized.

Attachment tube 14 may have optional modifications: (a) it may have side holes or U-shaped fenestrations to allow for overstenting of the lower renal artery, accessory renal arteries as well as mesentaric vessels, or even both renal arteries in short necks; (b) it may have larger gaps between stents for better adaptation for tortuous or shrinking necks, or both. In these instances, there is a need for a two-step trigger mechanism that keeps the tube restrained to a smaller diameter than the lumen dimension in order to make corrections to its position both rotationally or longitudinally.

Contralateral tube or leg 16 is associated with contralateral stump 24 and would be similar in size and shape to ipsilateral leg 22, having a primary diameter of about 12 mm, an overlap length of about 35 mm, a length to a flared distal end of about 50 mm, and a flared end of about 18 to 20 mm in diameter when unconstrained.

Intragraft tube 18 would be similar to attachment tube 14 but without an attachment stent like stent 50. Thus, it would have a diameter when unconstrained of about 26 to 30 mm, and would have a total length of about 50 to 80 mm. Intragraft tube 18 is shown deployed in FIG. 10.

Figure 7:
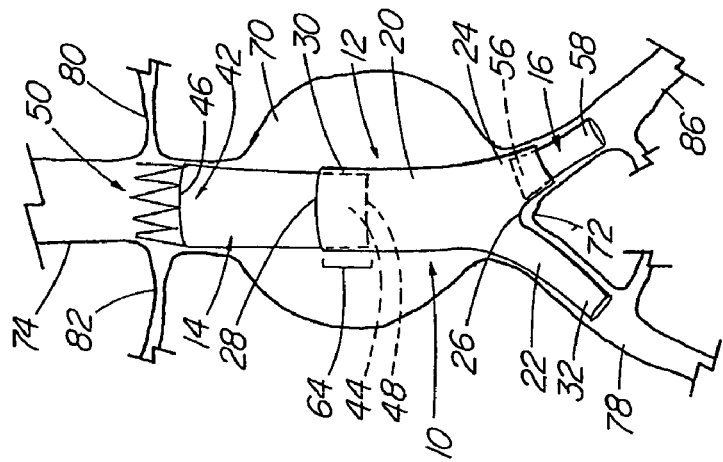
Figure 6:
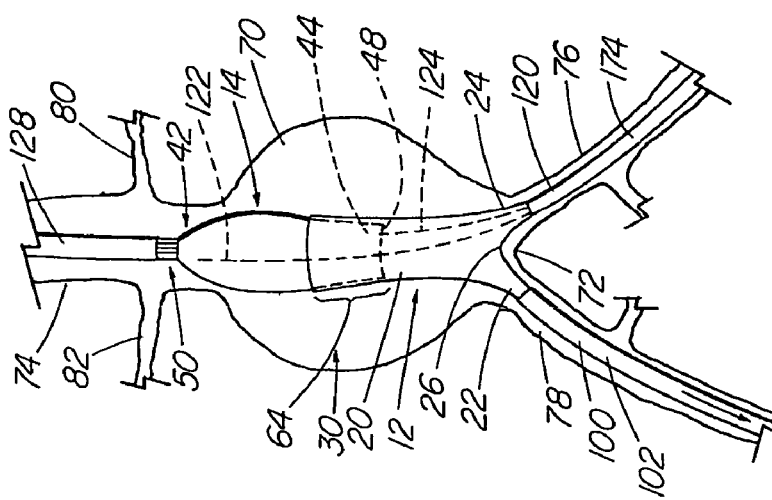
Figure 5:
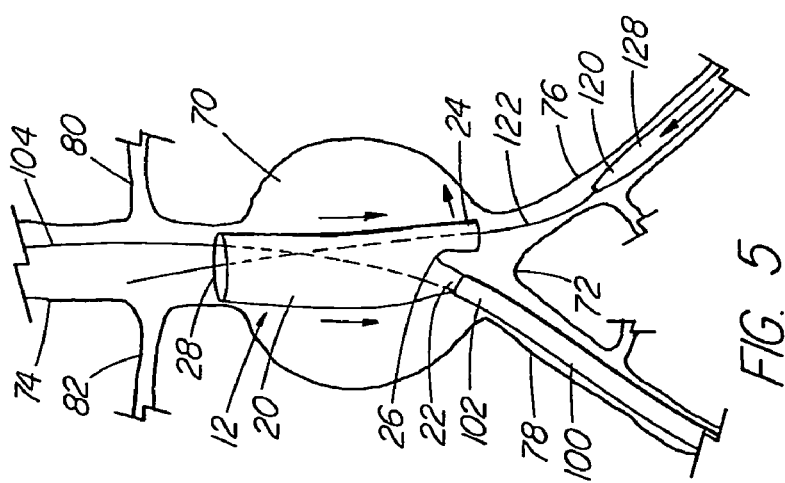

Now, with reference to FIGS. 5 to 7, general deployment of the stent graft assembly of the present invention will now be described. Delivery of the stent graft assembly to the site of the abdominal aortic aneurysm (AAA) 70 comprises the following steps:

1) position and partially deploy from the first delivery system 100 by way of first guide wire 104, the main stent graft tube 12 within the aneurysm 70, until the contralateral stump 24 is released from the sheath 102, while retaining the ipsilateral iliac limb 22 within the sheath of first delivery system 100 to maintain control (FIG. 5);

2) insert second guide wire 122 from second delivery system 120 into the contralateral stump 24 from the contralateral iliac artery 76, and pull the main stent graft 12 toward the bifurcation 72 of the aorta 74 within the aneurysm 70, for the crotch of bifurcation 26 of main stent graft body 12 to become seated on the bifurcation 72 (as in FIGS. 6 and 7) and for contralateral stump 24 to extend along contralateral iliac artery 76 while ipsilateral leg 22 extends along ipsilateral iliac artery 78;

3) determine the location of renal arteries 80,82 with respect to the vessel's bifurcation 72 and the proximal end 28 of the main stent graft body 12, and select the appropriate length of attachment tube 14 to be delivered to the main stent graft body for attachment at the proximal end thereof;

4) endovascularly introduce the second delivery system 120 by way of the contralateral iliac artery 76 along second guide wire 122, 5) deploy the attachment tube 14 at the renal arteries, as seen in FIG. 7, by first releasing distal end portion 44 from a first sheath 124 of delivery system 120 within proximal end portion 30 of main stent graft body 12 and then releasing attachment stent 50 from introducer or dilator 128, and inflating the balloon 170 (see FIG. 13) for modeling the attachment tube for expansion and vessel wall attachment by attachment stent 50;

6) deploy the contralateral leg 16 from within a second sheath 174 (see FIG. 13) of second delivery system 120 so that its proximal end expands within contralateral stump 24 (FIG. 7), then fully release cuff 58 into contralateral iliac artery 76;

7) fully deploy ipsilateral leg 22 within ipsilateral iliac artery 78 by withdrawing the sheath 102 of first delivery system 100, thus completing stent graft assembly 10; and 8) remove the delivery systems 100 and 120 for completion of the angioplasty.

Figure 9:
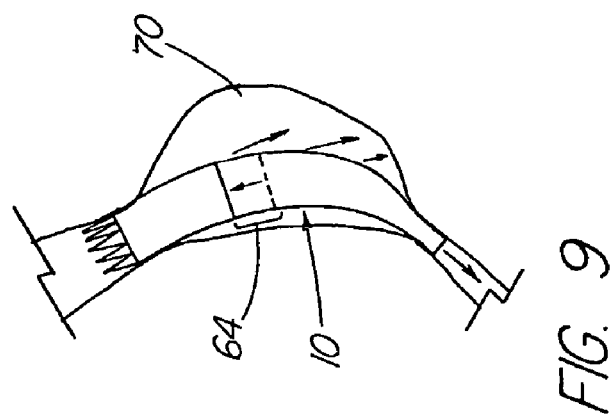
FIG. 9 shows a side view of an aneurysm having a stent graft of the present invention disposed therein.
Figure 8:
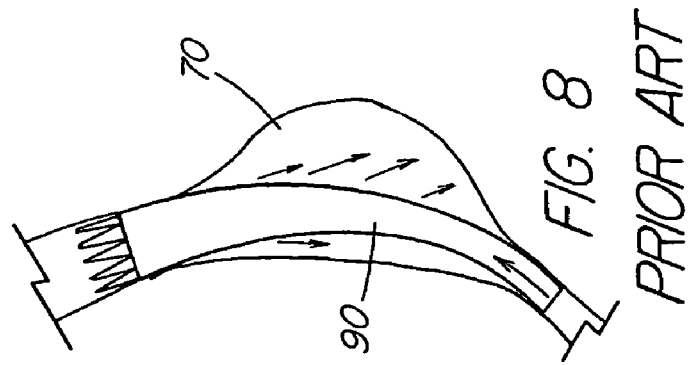
FIG. 8 shows a side view of an aneurysm having a representative Prior Art stent graft disposed therein.

FIGS. 8 and 9 generally depict forces upon a stent graft within an aneurysm 70 from blood flow after installation of a stent graft, with FIG. 8 illustrating the response of a conventional stent graft 90 while FIG. 9 illustrates the response of the stent graft 10 of the present invention. A stent graft deployed within an aneurysm most commonly is constrained to assume an arcuate shape. Blood flow from the proximal aneurysm entrance at the renal arteries toward the iliac arteries (indicated by the solid arrow) results not only in pressure on the bifurcation 36 (FIGS. 5 to 7) but also pressure on the convex side of the stent graft wall, tending to urge the convex side wall further in the convex direction as represented by the small arrows, and this results in pulling by the stent graft wall on the proximal and distal ends of the stent graft sufficiently stressing the stent graft-vessel wall attachments of the prior art stent graft 90 (also represented by small arrows) for at least one of the two ends to move toward the aneurysm. With the stent graft 10 of the present invention, the frictional engagement between the attachment tube and the main stent graft body 12 in the overlapping region 64 permits incremental movement in response to the stress such that neither the proximal nor distal ends of the stent graft become dislodged, nor is the stent graft explanted.

Figure 10:
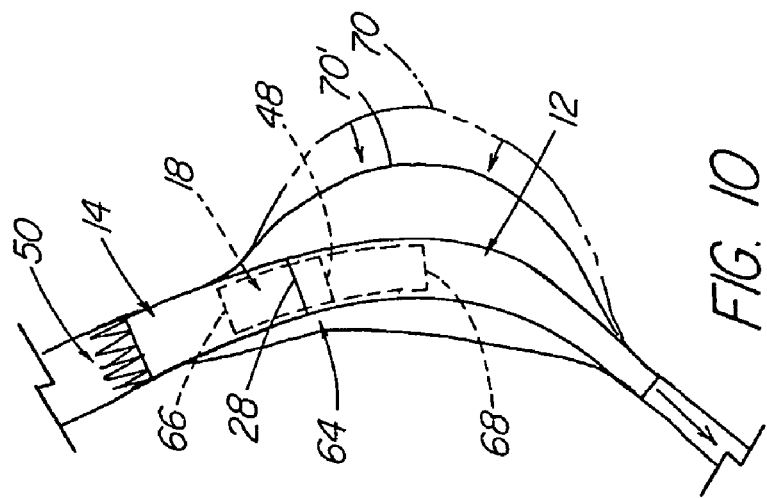
FIG. 10 illustrates the deployment of the intragraft tube within the stent graft, especially useful upon lengthening of the aneurysm during shrinkage thereof.

Intragraft tube 18 could be later deployed by a delivery system to underlie and support the overlapping region, so that it is positioned partially within both the main stent graft tube 12 and the attachment tube 14 as seen in FIG. 9. FIG. 10 depicts lengthening of an aneurysm site after installation of a stent graft, as the aneurysm 70 (in phantom) gradually shrinks to smaller sizes such as indicated by 70' and allowing the aorta walls eventually to generally assume their original pre-aneurysm length. Stent graft assembly 10 of the present invention is responsive to such lengthening by permitting incremental movement of the attachment tube 14 with respect to the main stent graft 12 at the overlapping region 64. Shown in FIG. 10 is intragraft tube 18 disposed within stent graft assembly 10 underlying and extending beyond the overlapping region 64 of the attachment tube 14 and main stent graft 12, with proximal end 66 and distal end 68 of intragraft tube 18 shown in phantom to be located beyond the ends of overlapping region 64. Intragraft tube 18 thus supports stent graft 10 spanning the overlapping region, and its self-expanding stents provide an expansive force outwardly such that the outer surface of tube 18 presses outwardly against and frictionally engages the interior surfaces of both attachment tube 14 and main stent graft 12 in a manner permitting incremental movement therebetween while assuring the continuity and integrity of the stent graft.

Figure 11:
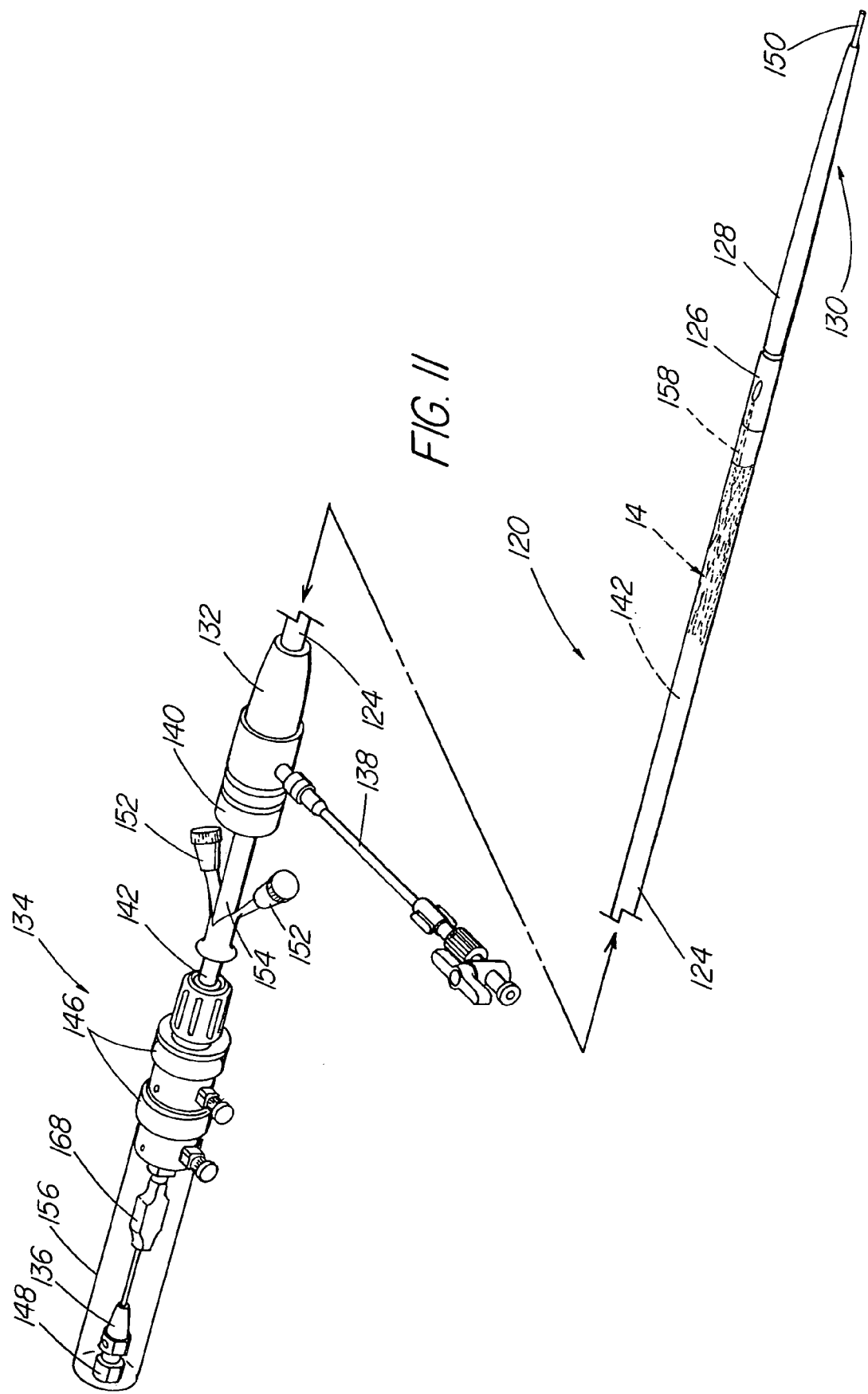
FIGS. 11 and 12 show the delivery system, with FIG. 12 showing the trigger wire controls included in the main body delivery system of FIG. 11.
Figure 12:
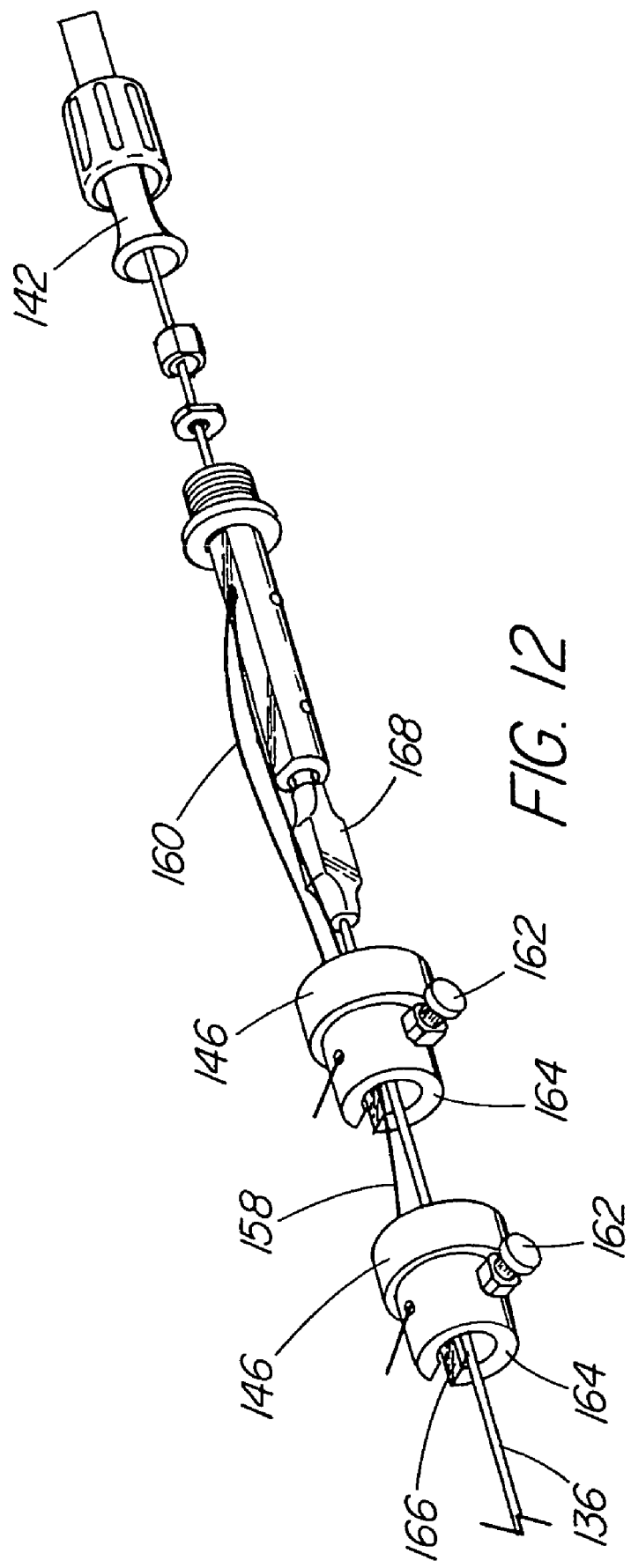

Referring to FIGS. 11 to 13, the delivery system 120 for the attachment tube 14 (and contralateral limb 16) will now be described, having a first (or outer) sheath 124, a top cap 126 and tapered dilator 128 at proximal end 130, and a fitting 132 at distal end 134 of the delivery system. Top cap 126 is affixed to the distal end of dilator 128, which is affixed at the proximal end of a small diameter inner cannula 136 that extends completely through the delivery system to a distal end. Fitting 132 is affixed to first sheath 124, and joined to the side of fitting 132 is injection system 138, for saturating the stent graft with anticoagulant heparin prior to deployment, and optionally for the injection of contrast medium thereafter. At the distal end of fitting 132 is a check-flow valve 140 through which extends pusher 142. Distally of pusher 142 is seen handle 144 of inner cannula 136, and trigger wire control systems 146.

Stylet 148 extends through inner cannula 136, through pusher 142 and first sheath 124 and top cap 126 to a proximal tip 150 that protrudes from the proximal end of the tapered dilator 128; stylet 148 is of protective value during shipping and handling but is removed prior to use in the medical procedure. Tabs 152 are provided at the distal end of short sheath 154, for peeling away the sheath prior to the medical procedure; sheath 154 protects the patency of the introducer lumen at the check-flow valve during shipping and handling, and extends only into fitting 132. For protection of the distal end components during handling, a protective tube 156 is secured therearound, and it also is removed prior to the procedure.

Trigger wire control systems 146 are shown in greater detail in FIG. 12. Control systems 146 for the two trigger wires 158,160 of the delivery system 120 each include a safety lock 162 that is removed laterally, and a release ring 164 that is moved distally (away from the patient) parallel to the inner cannula 136 and pulls the respective trigger wire out of the assembly. The trigger wire 158 for securing the attachment stent 50 of the attachment tube 14 against any axial movement until released, is first to be removed prior to being able to actuate the controls for trigger wire 160 that secures the distal end portion 44 of the attachment tube against any axial movement until released. Also, the release ring 164 for the distal end portion may be a different color than that for the attachment stent, to clearly indicate to the physician which trigger wire the particular control system actuates. The release rings 164 have axial slots 166 therealong to permit lateral removal from about the inner cannula 136. Pin vise 168 tightens upon and releases inner cannula 136 so that top cap 126 and dilator 128 can be advanced to deploy and be withdrawn for docking and system withdrawal.

Referring now to FIGS. 13 and 14, both the attachment tube 14 and the contralateral leg 16 would be loaded in second double sheath delivery system 120. In one arrangement, the second double sheath delivery system would include an inflation balloon 170 adjacent to the dilator, followed by the attachment tube 14 in the first or outer sheath 124, and the pusher for the attachment tube and the contralateral leg 16 and its pusher 172 all in the second or inner sheath 174. In a second arrangement shown in FIG. 14 having a smaller size, the attachment tube 14 would be adjacent the distal tip in the first sheath 124, and the balloon 170, the attachment tube pusher and the contralateral leg 16 and its pusher 172 would be in the second sheath 174.

Figure 15:
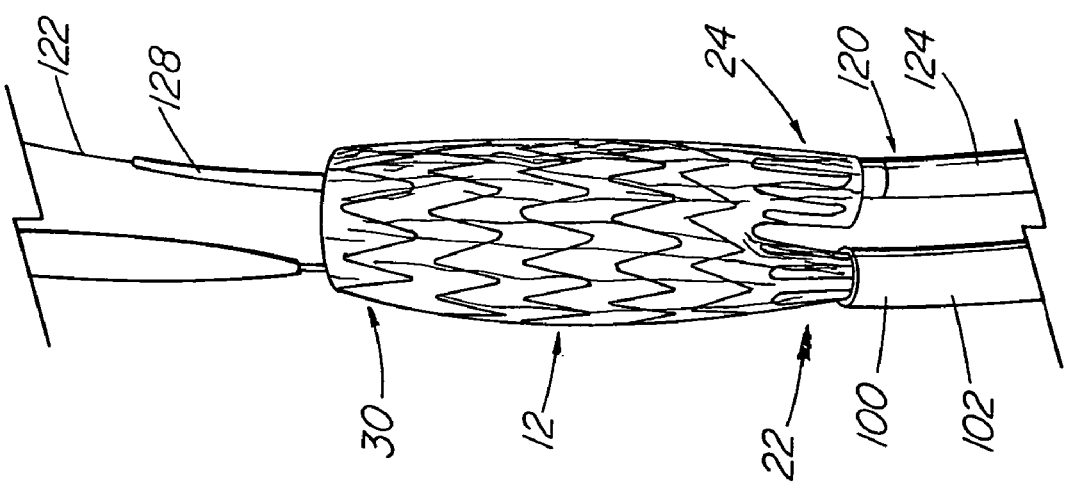

Deployment of the main stent tube body 12 and attachment tube 14 is more particularly shown in FIGS. 15 to 18. In FIG. 15, main stent graft body 12 has been partially deployed, with ipsilateral leg 22 still retained within sheath 102 of delivery system 100. Proximal end portion 30 has been released and has self-expanded. Second delivery system 120 has been inserted through contralateral stump 24 with dilator 128 extending beyond proximal end 28 along second guide wire 122.

Figure 17:
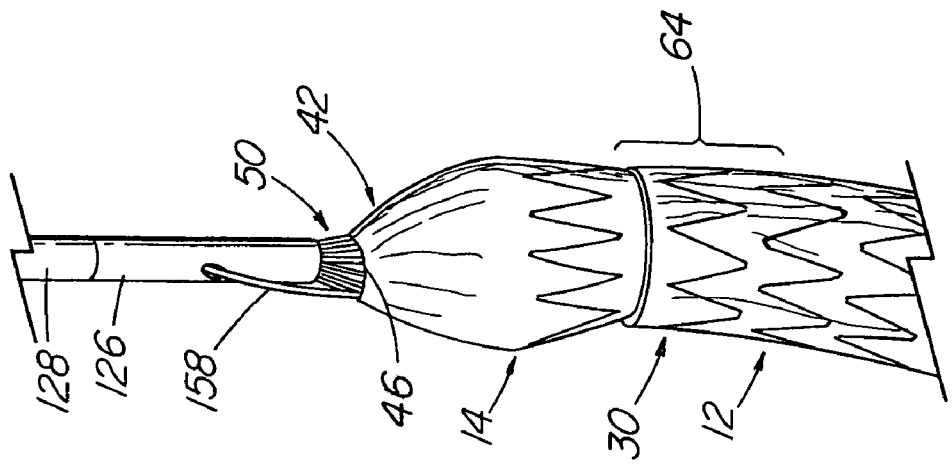
FIGS. 15 to 18 depict the sequential deployment of the main stent graft body and the attachment tube.
Figure 16:
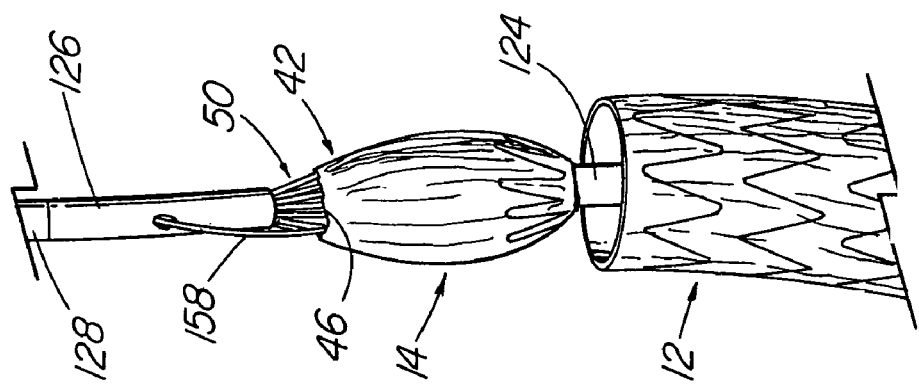
Figure 18:
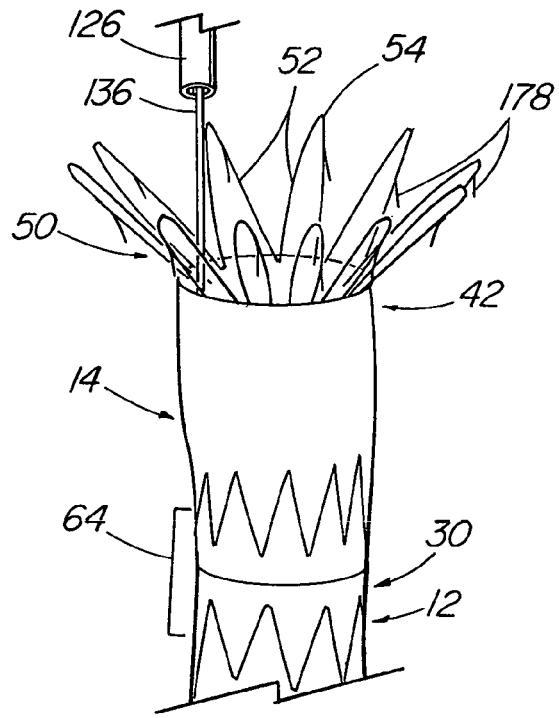
Figure 19:
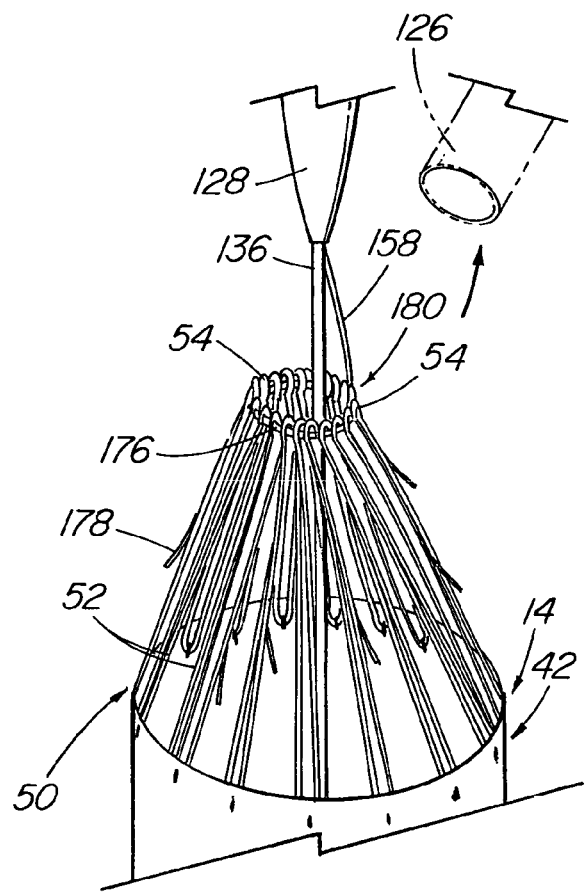
FIG. 19 is an enlarged view showing retention of the attachment stent prior to deployment.

Referring to FIG. 16, attachment tube 14 is seen being partially deployed from first sheath 124, with attachment stent 50 still restrained within the distal end of top cap 126 of dilator 128, and with proximal end 46 held closed by the top cap while the stent within the proximal end portion 42 is further held closed by trigger wire 158 and suturing 176 (see FIG. 19). In FIG. 17, the distal end portion 44 of the attachment tube has been pushed from first sheath 124 and has deployed within the proximal end portion 30 of main stent body 12, while attachment stent 50 remains restrained by dilator 128. FIG. 18 illustrates the ends 54 of struts 52 of attachment stent 50, after they have self-expanded upon release from top cap 126. Barbs 178 are affixed to struts 52 and will attach to vessel walls of the aorta upon full self-expansion.

Prior to deployment, the proximal end of the attachment stent 50 may be held closed by top cap 126 of the dilator, as shown in FIGS. 16 and 17, which is withdrawn from the attachment tube when properly positioned, as is conventionally used with some stent grafts; or as preferred, it may be held closed by trigger wire and sutures, as disclosed in WO 98/53761, actuatable from controls at the distal end external to the patient. With reference to FIGS. 19 and 20, trigger wire 158 is disposed within a small-diameter inner cannula 136 extending through the delivery system and includes a proximal release end 180 within the top cap 126, that initially extends through a loop at the end 54 of one of the pairs of joined struts 52 of the attachment stent 50, holding the stent loop against the small-diameter cannula. A suture 176 extends from the trigger wire release end 180 to two or more of the other loops of the attachment stent to initially maintain the proximal end of the stent 50 gathered in a closed position. Upon actuation of the trigger wire controls (FIG. 12), the wire is withdrawn from the stent loop and the suture 176 allowing the stent proximal end to self-expand. A similar trigger wire system preferably is used to secure the stent at the distal end portion 44. Such a system may also be used with delivery system 100 to deploy at least the proximal end portion 30 of the main stent graft body.

In FIGS. 18 to 20, the trigger wire 158 is shown in detail in relationship to attachment stent 50 of attachment tube 14. FIG. 19 illustrates attachment stent 50 before top cap 126 has been placed over the exposed struts 52, during which a suture holds the strut ends 54 gathered near the inner cannula; the suture is removed once the top cap is in place. Trigger wire 158 extends from its control section 146 along inner cannula 136 of the delivery system 120 within pusher 142, and includes a release end 180 that extends outwardly through an aperture of proximal pusher body 182 and forwardly through attachment tube 14 and then outwardly thereof near proximal end 42 thereof, then forwardly and into a small aperture of the top cap and through a loop at the joined proximal ends 54 of a pair of struts 52 and then further into the dilator, held therein by friction fit by the inner cannula threaded into the dilator. Release end 180 of trigger wire 158 holds the exposed struts of the attachment stent within the top cap, fixed against axial movement with respect to the top cap and dilator. Top cap 126 surrounds all the exposed struts 52 of attachment stent 50 when the attachment tube 14 is delivered to the site of the ruptured aneurysm, until it is accurately positioned at the aneurysm neck.

First sheath 124 is then pulled distally with respect to attachment tube 14 by manual movement of fitting 132 while the struts of the attachment stent are held within and still restrained within top cap 126, as seen in FIGS. 18 and 20, after which trigger wire 158 is pulled from the top cap and withdrawn completely from the catheter, thus releasing the loop of the attachment stent struts. With the attachment tube held against axial movement relative to pusher 142 by trigger wire 160, the dilator/topcap/cannula subassembly is pushed forwardly (proximally) by pushing forwardly on cannula handle 144 to release the attachment stent 50, whereupon the ends 54 of struts 52 self-expand radially outwardly to engage the vessel wall, and barbs 178 seat into the vessel wall to thereafter secure the attachment tube 14 in its desired position. Such a trigger wire system is disclosed in WO 98/53761. Optionally, a molding balloon may be used to inflate within self-expanded attachment stent 50 to assuredly press the struts against the vessel wall and seat the barbs.

Similarly, as shown in FIG. 20, the second trigger wire 160 secures the distal end portion 44 of attachment tube 14 against any axial movement as the top cap 126 is being urged forwardly from attachment stent 50 which would tend to pull the attachment stent and the main body due to friction. Trigger wire 160 includes a release end 184 that first extends outwardly from proximal pusher body 182 and along groove 186, then inwardly through the graft material of the distal end portion 44 and through a stent end loop and into an opening in the proximal pusher body, and then forwardly along inner cannula 136 where it is held in a force fit thereagainst by the proximal tip of pusher 142. Then, upon actuation of the control system 146 for trigger wire 160, trigger wire 160 is pulled from the delivery system which releases the distal end portion 44 of the attachment tube 14 which then fully self-expands within the aneurysm toward the vessel wall.

Proximal pusher body 182 is then pushed proximally through now-deployed attachment tube 14 to abut against the distal end of the top cap 126; the abutment portion of proximal pusher body 182 has an outer diameter the same as the distal end of the top cap. The configuration of proximal pusher body 182 is shown in FIG. 20. Upon pulling the dilator/topcap/cannula subassembly distally, and in turn upon moving proximal pusher body 182 distally, tapered surfaces of the distal end (not shown) of the proximal pusher body gently engage and deflect radially outwardly any portions of the stents of the main body to prevent any stubbing or snagging that otherwise would occur by engagement of the top cap distal end were it to be exposed when pulled distally through the now-deployed attachment tube 14. Proximal pusher body 182 similarly has tapered surfaces 188 at its proximal end that gently engage and deflect outwardly any stent portions when it is pushed proximally through the main body to abut top cap 126.

Figure 21:
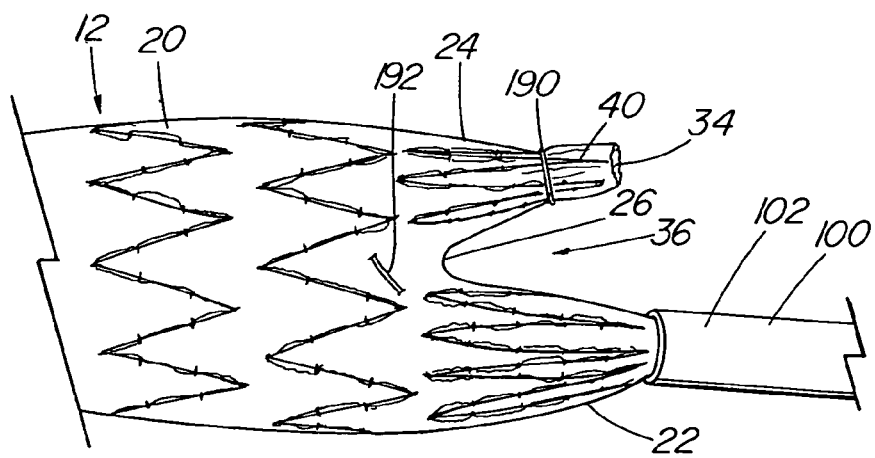
FIG. 21 is an enlarged view of the distal end portion of the main stent graft body illustrating maintaining the contralateral stump in a closed condition during placement of the main stent graft body.

As an option, the contralateral stump 24 of the main stent graft body 12 may be sutured to an initially closed position so that the main stent graft body may easily be pulled against the bifurcation 26. As shown in FIG. 21, the suture 190 extends through the loops of the stent 40 disposed along the outer surface of the contralateral stump's distal end 34, and is released after positioning by actuation of another trigger wire 192.

With the present invention are the following attendant advantages:

1) it has a modular concept for optimal on-site adaptation to a particular aneurysm site;

2) the use of an attachment tube with the main stent graft fills the entire length of the abdominal aortic aneurysm and gives the stent graft more stability;

3) the attachment tube enables the largest possible overlapping coextension, which increases stability and gives more safety by way of the resultant double wall, even in case of fabric tear;

4) the overlapping coextension at the same time allows freedom for the stent graft to adjust: the top of the graft assembly will not be pulled down by blood flow after placement, and the bottom part will be pushed down against the aortic bifurcation; and 5) the intragraft tube further assures the integrity of the stent graft and its ability to adjust incrementally as the aneurysm changes length.

The new concept was developed upon observation of the largest and closest follow up of first and second generation stent grafts. It is the first time that a graft design is modified extensively according to clinical experience with graft configuration changes and resulting complications. At the same time the new concept allows the advantage of extensively clinically tested components like stainless steel or nitinol stents, Dacron weave, and conformity. The new concept uses proven components in a modified manner that is based on the most extensive documentation and clinical analysis and most profound understanding of late graft behavior and changes in man.

With present-day systems, the increased precision and improved long term safety is at the price of a larger introducer system at the contralateral site, requiring surface dissection. With the long tapered nose cone-tip of the present invention, the contralateral artery can be punctured for insertion of the second double-sheath delivery system and the artery needs less dissection, just for clamping during direct suture. Attempts can be made to reduce the introducer sheath by total removal or repositioning the dilatation balloon, which confines packing space.

Weave and stent material may be thinner. The new concept of overlapping tubes allows probably the attachment and inner one to be less rigid and thinner. Weave probably can be made thinner and more porous per the inner tube at least, in the future. A new weave-generation could be tested thereby clinically in this position without the use of silk. Tears can easily be repaired by placement of a second tube later.

What is claimed is:

1. A delivery system for endovascular devices, comprising:
a first sheath having a distal end and a proximal end and containing at least a first expandable device at a proximal end;
  a second sheath movable within the first sheath and having a respective distal end and a respective proximal end, the respective proximal end concluding distally of the first expandable device and containing a second expandable device;

the first expandable device and the second expandable device being separate rate and separately deliverable from the delivery system, a first pusher associated with the first expandable device extending thereto within the first and second sheathes from a first proximal control pusher end exposed at the distal ends of the first and second sheathes; and a second pusher associated with the second expandable device extending thereto within the first and second sheathes from a second distal control pusher end exposed at the distal ends of the first and second sheathes.

2. A delivery system for endovascular devices as in claim 1 wherein the first expandable device comprises an attachment graft tube having proximal and distal end portions and defining a lumen therethrough and further including an attachment stent extending proximally from the proximal end portion.

3. A delivery system for endovascular devices as in claim 2 wherein the second expandable device comprises a contralateral leg extension.

4. A delivery system for endovascular devices as in claim 1 wherein the second sheath comprises an inflation balloon therein.

* * * * *